United States Patent [19]

Rabo et al.

[11] 4,242,103

[45] Dec. 30, 1980

[54] CYCLIC TWO STEP PROCESS FOR PRODUCTION OF METHANE FROM CARBON MONOXIDE

[75] Inventors: Jule A. Rabo, Armonk; Louis F. Elek, Peekskill, both of N.Y.; James N. Francis, Houston, Tex.

[73] Assignee: Union Carbide Corporation, New York, N.Y.

[21] Appl. No.: 45,319

[22] Filed: Jun. 4, 1979

Related U.S. Application Data

[63] Continuation-in-part of Ser. No. 889,558, Mar. 23, 1978, abandoned.

[51] Int. Cl.$^3$ .............................................. C10K 3/04
[52] U.S. Cl. .................................... 48/197 R; 48/210; 48/DIG. 6; 166/267; 252/421; 260/449 M; 260/449.6 M; 585/733
[58] Field of Search ............... 48/197 R, 210, DIG. 6; 252/411 R, 420, 421; 260/676 R, 449 M, 449.6 M; 585/733; 423/415 R, 439, 447.3, 459; 166/267

[56] References Cited

U.S. PATENT DOCUMENTS

| | | | |
|---|---|---|---|
| 2,686,819 | 8/1954 | Johnson | 585/733 |
| 3,031,287 | 4/1962 | Benson et al. | 48/197 R |
| 3,988,262 | 10/1976 | Andersen et al. | 260/449 M |
| 3,988,263 | 10/1976 | Hansford | 260/449 M |
| 4,032,556 | 6/1977 | Banks | 260/449 M |

OTHER PUBLICATIONS

"Disproportionation of CO Over Cobalt and Nickel Single Crystals", Renshaw et al., Journal of Catalysis, 22, 394-410, (1971).

Primary Examiner—Peter F. Kratz
Attorney, Agent, or Firm—Alvin H. Fritschler

[57] ABSTRACT

Carbon monoxide-containing gas streams are passed over a catalyst capable of catalyzing the disproportionation of carbon monoxide so as to deposit a surface layer of active surface carbon on the catalyst essentially without formation of inactive coke thereon. The surface layer is contacted with steam and is thus converted to methane and $CO_2$, from which a relatively pure methane product may be obtained. Dilute carbon monoxide-containing streams, as from underground coal gasification with air or the effluent from blast furnace operations, can be used without pretreatment to convert the carbon monoxide and/or to separate inert gases therefrom. Conversion of the active surface carbon with high pressure steam enables a high pressure product methane stream to be generated without expensive compression equipment and high energy consumption. Nickel, cobalt, iron, ruthenium, rhenium and alloys thereof are preferred catalysts, with the surface area thereof being preferably at least about 10 m$^2$/gr. Conversion of the active surface carbon can also be accomplished by contact with hydrogen.

62 Claims, No Drawings

CYCLIC TWO STEP PROCESS FOR PRODUCTION OF METHANE FROM CARBON MONOXIDE

REFERENCE TO RELATED APPLICATION

This application is a continuation-in-part of applicants' earlier filed application, Ser. No. 889,558, filed Mar. 23, 1978, now abandoned, entitled "METHANATION OF CARBON MONOXIDE WITHOUT PRIOR SEPARATION OF INERT GASES."

BACKGROUND OF THE INVENTION

1. Field of the Invention

The invention relates to the production of methane from carbon monoxide. More particularly, it relates to a methanation process capable of effectively utilizing dilute carbon monoxide-containing gas streams.

2. Description of the Prior Art

The catalytic hydrogenation of carbon monoxide to form methane is one of the most well known and established hydrogenation reactions.
This reaction, which is:

$$CO + 3H_2 \rightarrow CH_4 + H_2O, \qquad (1)$$

utilizes a synthesis gas, as from the gasification of coal with oxygen and steam, that is treated to provide a desired $H_2/CO$ ratio and to remove excess $CO_2$ and deleterious impurities such as sulfur compounds. As the $H_2/CO$ ratio of the raw synthesis gas is substantially below the necessary minimum ratio of 3/1, at least a portion of the carbon monoxide in the gas is generally first reacted with steam, over an iron or other suitable catalyst in the well-known "water shift" reaction, as follows:

$$CO + H_2O \rightarrow CO_2 + H_2. \qquad (2)$$

Excess $CO_2$ in the gas stream is removed by conventional means, such as by treatment with alkaline absorbents. Sulfur impurities are also removed to substantially under 5 ppm, e.g., to less than about 1 ppm, preferably to less than 0.2 ppm, to protect the methanation catalyst from poisoning by such sulfur impurities.

The water shift reaction normally does not go to completion, with the equilibrium determined by the reaction temperature and other operating conditions limiting the degree of completeness of the reaction. The desired $H_2/CO$ ratio is obtained, to achieve maximum utilization of the available CO and hydrogen, either by very careful choice and control of the processing conditions or by the treatment of a portion of the raw synthesis gas to produce a $H_2/CO$ ratio substantially in excess of 3/1 and blending the treated gas with the untreated portion to produce the desired $H_2/CO$ ratio.

One variation of the latter approach is disclosed in the Muller patent, U.S. Pat. No. 3,854,895, in which the primary gas from coal gasification is divided into two streams, one of which is subjected to water shift and subsequent methanation stages, the untreated stream being added to said treated gas successively during said methanation stages. Numerous prior art techniques also exist, it should be noted, for the production of methane from other gases containing hydrogen and carbon oxides. Humphries et al, U.S. Pat. No. 3,511,624, for example, relates to the two-stage production of a gas containing a high proportion of methane from a reaction mixture comprising hydrogen, carbon monoxide and dioxide, steam and at least 25% by volume methane.

Despite the established nature of the major steps in the known techniques for the gasification of coal and in the methanation of the resulting synthesis gas, improved processes for the production of methane are urgently needed to enhance the overall economics of methane production and/or to enable its production from carbon-monoxide-containing gas streams that cannot presently be used in a commercially feasible manner for the production of methane. This need is highlighted by the diminishing supply of natural gas and the recognized need to develop economical supplies of synthetic natural gas to meet existing and anticipated requirements for low-cost, high BTU gaseous heating fuels.

In the processing of synthesis gas obtained by the gasification of coal with oxygen and steam, pretreatment by the catalytic water shift reaction is a major processing step prior to methanation. This necessary adjustment of the $H_2/CO$ ratio adds, of course, to the overall processing costs and necessarily reduces the amount of carbon monoxide available for conversion to methane. In addition, gas streams containing a low concentration of carbon monoxide and/or a high concentration of inert gases are generally not suitable for methanation purposes because of the costs associated with the concentration of the carbon monoxide, as by cryogenic or absorption means. For example, the effluent from the underground gasification of coal with air is not a suitable feed gas for conventional methanation techniques because of the high proportion of inert gases, i.e., nitrogen, in said effluent. Similarly, the effluent from blast furnace operations contains a high proportion of nitrogen and is not suitable for the economic production of methane because of the prohibitive cost of concentration the carbon monoxide content thereof.

Conventional processing techniques, in addition, are known to have particular operating difficulties, the overcoming of which tends to shift the equilibrium and reduce the yield of desired methane product or tends to reduce the overall efficiency of the production reaction. The Muller patent referred to above, i.e., U.S. Pat. No. 3,854,895, thus discloses that the formation of free carbon by the Boudouard reaction is promoted by an increase of CO in the reaction mixture, leading the prior art to employ excess hydrogen and to obtain not pure methane but a mixture of methane and hydrogen. The above-mentioned Humphries et al patent, U.S. Pat. No. 3,511,624, likewise refers to said Boudouard reaction:

$$2CO \rightarrow CO_2 + C \qquad (3)$$

and discloses the known use of steam to react with a portion of the CO in the gas stream per reaction (2) above to assure the presence of sufficient $CO_2$ to prevent the Boudouard reaction from moving to the right and causing carbon desposition, the process including the removal of the resulting carbon dioxide and any remaining steam from the mixture. While the problem of undesired carbon deposition is thus avoided in the art, the necessary adjustments to achieve this result create a further incremental limitation on the processing economy and flexibility of the prior art techniques for methane production. For practical commercial operations, it is highly desirable in the art that, without such limitations, a methanation process be developed that can be operated on a continuous cyclic basis without undue loss of catalyst efficiency and without a need for continuous catalyst regeneration as a necessary step of the cyclic methanation process.

It is an object of the invention, therefore, to provide an improved process for the production of methane.

It is another object of the invention to provide a process for the low-cost production of methane from carbon monoxide-containing gas streams.

It is another object of the invention to provide a process for the production of methane from dilute carbon monoxide-containing gas streams without the necessity for preliminary concentration of the carbon monoxide in said gas streams.

It is another object of the invention to provide a process for the enhanced catalytic production of methane from carbon monoxide-containing gas streams on a cyclic basis without requiring catalyst regeneration as a necessary step of the cyclic process.

It is a further object of the invention to provide a process for the production of methane from the effluent of the underground gasification of coal with air.

It is a further object of the invention to provide a process for the production of methane from the effluent from blast furnace operations.

With these and other objects in mind, the invention is hereinafter described in detail, the novel features thereof being particularly pointed out in the appended claims.

SUMMARY OF THE INVENTION

The invention utilizes the catalytic disproportionation of carbon monoxide to carbon and carbon dioxide to deposit a surface layer of active surface carbon on the surface of a catalyst, at about 100°–400° C. and 1–100 atmos., essentially without the subsequent formation of inactive coke thereon. The layer of active surface carbon is thereafter contacted with steam, at about 100°–400° C. and 1–100 atmos., thus converting the active surface carbon to methane and carbon dioxide. In a less desirable embodiment, the surface layer may be contacted with hydrogen rather than with steam. No concentration of carbon monoxide and/or separation of inert gases is required prior to the use of dilute carbon monoxide-containing streams in the practice of the invention. At least about 12.5% and up to nearly 25% of the carbon in said carbon monoxide decomposed on the catalyst is recovered in the form of relatively pure methane. The presence of hydrogen or water in the carbon monoxide-containing feed gas stream results in methane formation upon initial contact of the feed gas with the catalyst. This methane in the gas vented from the surface layer of active surface carbon can be effectively utilized in a combustion zone for the generation of heat for steam production or other energy recovery purposes. Catalyst materials, such as nickel, cobalt, iron, ruthenium, rhenium and alloys, thereof, capable of catalyzing the disproportionation of carbon monoxide may be employed, generally in combination with catalyst support additives and/or binders to assure that the catalyst has a desired combination of activity, capacity and stability for practical, commercial operations. By carrying out the conversion of active surface carbon with high pressure steam, a product stream of high pressure, relatively pure methane is produced without the necessity for employing expensive compression equipment and incurring a large consumption of energy for compressive purposes. For enhanced methanation in practical commercial operations, a cyclic, essentially two-step process is desirable, with the disproportionation catalyst being employed in such cyclic, two-step operations without the need for regenerating the catalyst as a necessary additional step of the cyclic process. Especially preferred catalysts for such cyclic operations are nickel, cobalt, ruthenium, rhenium and alloys thereof, in the metal state. For practical commercial operations, it is especially preferred that the CO disporportionation step be carried out at temperatures of from about 200° C. up to about 350° C., and that the active surface carbon deposited on the catalyst be reacted with steam for conversion to produce methane and carbon dioxide.

DETAILED DESCRIPTION OF THE INVENTION

The invention enables dilute carbon monoxide-containing gas streams, unacceptable for use by known processes, to be effectively and efficiently utilized for the economic production of methane. Separation of the carbon monoxide from inert gases present in such dilute carbon monoxide-containing streams is accomplished, in the practice of the present invention, without economic disadvantage vis-a-vis known processes applicable to carbon monoxide-containing gas streams not containing appreciable quantities of inert gases. The present invention is of significance, therefore, not only as a process for the production of low-cost methane but as a process uniquely capable of utilizing carbon monoxide available in gas streams not previously suitable as feed streams for the commercial production of methane.

The invention includes the passing of a carbon monoxide-containing gas stream over a suitable catalyst under conditions such that the carbon monoxide is decomposed to form carbon dioxide and active surface carbon, designated as C* and deposited as a surface layer on said catalyst, according to the reaction:

$$2CO \rightarrow CO_2 + C^*. \tag{4}$$

The carbon dioxide and inert gases present in the feed stream are vented from the surface layer of active surface carbon, which is thereafter converted to methane by contact with steam as follows:

$$2C^* + 2H_2O \rightarrow CH_4 + CO_2. \tag{5}$$

The carbon efficiency of the process can be illustrated by the overall reaction (6) below that represents the total of reactions (4) and (5) as performed in the practice of the present invention:

$$4CO + 2H_2O \rightarrow 3CO_2 + CH_4. \tag{6}$$

Thus, 4 moles of CO are required for the production of one mole of methane in the stoichiometric relationship illustrated by reaction (6). The present invention is capable of recovering methane in amounts representing at least about 50% of the stoichiometric amount and, in preferred embodiments, at least about 80% and up to nearly 100% of said stoichiometric amount. Upon separation from the accompanying $CO_2$ by conventional means, therefore, methane is recovered in the form of a low-cost, relatively pure product with the carbon values thus recovered being at least about 12.5% and up to nearly 25% of the carbon present in the carbon monoxide decomposed upon contact with the disproportionation catalyst.

Gas streams containing from about 1 to 100% by volume carbon monoxide can be utilized as the feed stream in the practice of the invention. As indicated above, the invention is uniquely capable of utilizing carbon monoxide in gas streams not suitable for known methanation techniques because of relatively high concentrations of inert gases therein. Gas streams containing carbon monoxide in amounts of from about 5% to about 50% by volume and containing at least about 5% by volume of nitrogen represent sources of carbon monoxide not previously suitable for commercial methanation operations that are highly suitable for use in the process of the invention. Those skilled in the art will readily appreciate that the gas streams should be sufficiently free from catalyst poisons to ensure adequate catalyst lifetimes. Thus, sulfur impurities should be present in very low concentrations, e.g. less than 1 ppm, preferably less than 0.2 ppm. Conventional techniques not forming a part of this invention are available in the art for removing sulfur impurities as required. If hydrogen or water vapor is also present in the feed gas stream, such gases may be converted, partially or completely, to methane by reaction with carbon monoxide under the reaction conditions. The carbon monoxide remaining after said reaction with hydrogen or water vapor will be decomposed to active surface carbon and carbon dioxide in accordance with reaction (4) above. For this reason, the hydrogen and water vapor will preferably be present in the feed gas stream in quantities less than 10% by volume of the amount of carbon monoxide present in the gas stream. It is within the scope of the invention, however, to effectively utilize any methane formed during the carbon monoxide decomposition step for heat generation purposes enhancing the overall economics of the low-cost methanation process of the invention. This aspect of the invention is discussed further hereinbelow.

The carbon monoxide decomposition step, in which the carbon monoxide present in the feed gas stream is decomposed to form a surface layer of active surface carbon deposited on a disproportionation catalyst, effectively serves to concentrate the carbon values to be converted to methane, regardless of the carbon monoxide content of the feed gas stream. Dilute carbon monoxide-containing gas streams can be readily employed, therefore, without the necessity for the prior concentration of the carbon monoxide as would be required in conventional techniques. The venting of the carbon dioxide formed as a result of carbon monoxide decomposition, together with the inert gases that may be present in the gas stream, from the catalyst having the surface layer of active surface carbon values to be converted to methane from said gases is readily carried out as an incidental unit operation procedure prior to said active surface carbon conversion in the second chemical step of the essentially two-step process of the invention. The use of a dilute carbon monoxide-containing gas stream in the process of the invention thus does not require the prior separation of the carbon monoxide content thereof from inert gases as would be required in conventional methanation techniques. This ability to utilize dilute carbon monoxide-containing gas streams constitutes a major advance in the art, permitting the production of low-cost methane from gas streams not capable of practical utilization for the economic production of methane by presently available techniques.

The decomposition of carbon monoxide over a disproportionation catalyst is carried out at a reaction pressure of from about 1 to about 100 atmospheres and at a reaction temperature of from about 100° C. to about 400° C., preferably between about 200° C. and about 300° C. with space velocities of from about 1000 to about 30,000 $hr^{-1}$. Since the most useful product of the carbon monoxide decomposition, for purposes of the invention, is the solid surface layer of active surface carbons, it will usually be or no advantage to carry out the decomposition reaction at pressures much above atmospheric. The carbon monoxide-containing gas stream is passed over the catalyst for a time sufficient to deposit a surface layer of active surface carbon on the catalyst essentially without the formation of inactive coke thereon. Such inactive coke is not only itself inert under the methanation reaction conditions of the invention, but may tend to reduce the capacity of the catalyst to form active surface carbon in subsequent operations. For practical commercial applications of the invention, such subsequent operations, involving the use of the catalyst for the disproportionation of additional quantities of CO, are desirably carried out at reaction temperatures above about 100° C. and preferably within said preferred range of from about 200° C. to about 300° C. or even higher up to about 350° C. It will be understood that said CO disproportionation temperature refers to the average temperature of the reaction bed. It will also be understood by those skilled in the art that the particular reaction temperature pertaining to any given commercial application of the invention will be subject to inevitable variations depending on the type of operation employed, e.g. fixed or fluid bed, and on the capability of temperature control equipment employed in such commercial application of the invention. The reaction temperature may exceed the indicated preferred temperature limits on a transitory basis without departing from the scope of the invention although, for enhanced economic and technical practicability of commercial applications, the average reaction bed temperature should desirably be within the preferred range indicated above, i.e. from about 100° C., most preferably from about 200° C. up to about 350° C. At higher temperatures, the suitability of the catalyst for use in the cyclic two-step process of the invention is diminished so that the overall efficiency of the process is adversely effected, and the cost thereof increased, at such less favorable operating conditions.

It should be noted that the active surface carbon formed in the practice of the invention is quite distinct from the inactive coke formed if the carbon monoxide decomposition is allowed to proceed beyond the maximum level of active surface carbon deposition. As indicated by the references to carbon deposition in the prior art description above, such inactive coke is known in the art as an undesired potential deposit on catalyst surfaces from carbonaceous feeds employed in various methanation operations. Such coke has essentially the reactivity of graphitic carbon. Its reaction with steam, for example, requires temperatures in the range of from about 600° C. to about 1000° C. This reaction, which is the well-known water gas reaction, produces CO and $H_2$ as its principal products. The active surface carbon of the present invention, on the other hand, reacts with steam at appreciably lower temperature levels to provide methane as its principal product in accordance with equation (5) above. While the prior art is concerned with the avoidance of the undesired deposition of inactive coke on catalytic surfaces, the present invention utilizes the deposition of active surface carbon, without formation of inactive coke, to produce methane by a novel, low-cost process as described herein.

The amount of active surface carbon deposited will depend upon the surface area of the disproportionation catalyst and the operating conditions employed. Relatively low temperatures and the shortest possible residence time tend to favor the formation of the active surface carbon. Under some circumstances, particularly at higher temperatures within the operable range or with a very long residence time, the presence of CO in the gaseous effluent denotes a relatively sharp demarcation point between the deposit of the desired active surface carbon and the undesired deposition or other formation of inactive coke on the surface of the catalyst. In determining the amount of active surface carbon that can be deposited on the catalyst, therefore, the point at which CO breakthrough occurs can be taken as a practical indicator of the maximum level of active surface carbon deposition. It will be understood, however, that said maximum level of deposition must be determined, for any particular embodiment, by the particular operating conditions employed, the specific catalyst utilized and the available surface area of the catalyst as applied in such embodiment.

The invention utilizes a catalyst capable of catalyzing the disproportionation of carbon monoxide. The transition metals including and to the left of nickel in the third row of the Periodic Table; including and to the left of rhodium in the fourth row thereof; and including and to the left of iridum in the fifth row thereof are capable of catalyzing said disproportionation. Preferred catalysts include nickel, cobalt, iron, ruthenium, rhenium and alloys thereof, with nickel and cobalt being most preferred on an overall technical-economic basis. For purposes hereof, it will be understood that the catalyst shall include the metallic form, the oxide form, or any other suitable form of the particular catalyst employed. As the active surface carbon will be deposited in a surface layer while assuring that the decomposition reaction does not proceed to the point of inactive coke formation, a high catalyst surface area is advantageous to achieve a high surface carbon loading, enhancing the economics of the process. The catalyst employed will preferably have a surface area of at least about 10 $m^2/gr$, with surface areas of at least about 25 $m^2/gr$ being more preferred. In some embodiments, the catalyst may have an even higher surface area, i.e. of at least about 50 $m^2/gr.$, it being appreciated that such high surface areas contribute to the attractiveness of the invention on an overall technical and economic basis. It will also be appreciated that the catalyst will generally be employed in combination with catalyst support additives and/or binding agents to assure that the catalyst has and maintains a desired combination of activity, capacity amd stability for use in practical fixed or fluid bed commercial operations. It will also be understood that the surface area of the catalyst, as referred to herein, relates to the B.E.T. surface area of the catalyst composition measured after the combination of the catalyst with such additives or agents and after reduction of the catalyst to its active state.

For the economic production of methane in practical commercial operations, it is highly desirable that the catalyst be capable of use in the essentially two-step, cyclic, low-cost process of the invention without the need for regeneration following each reaction cycle. Furthermore, the catalyst should advantageously be capable of effective continued use in the cyclic two step process of the invention over as long a cycle period as possible prior to regeneration to enhance the economic feasibility of the process in such commercial operations. For such cyclic operations that are inherently part of the economic attractiveness of the invention, the catalyst will, in particularly preferred embodiments, be employed essentially in its metal state and will be taken from especially preferred catalysts, including nickel, cobalt, ruthenium, rhenium and alloys thereof, with nickel and cobalt being most preferred on an overall technical-economic basis to enhance the cyclic feature inherent in the overall advantages of the two step process of the invention. It will be understood by those skilled in the art that such catalysts, in their metal state, are not generally available in a totally pure form but may contain small amounts of oxygen. The especially preferred catalysts enhancing the cyclic, two step process of the invention will be substantially in the metal state rather than in oxide form. It will be noted that iron is not included among the especially preferred catalysts for practical commercial operation of the two step, inherently cyclic process of the invention, since iron is considerably less reactive to CO in the initial disproportionation step than is the most preferred nickel and cobalt catalysts. In the active surface carbon conversion step, the iron is found to react with steam to form an oxide that may be inert or relatively inactive for carbon monoxide disproportionation depending on the valance state of the iron in said oxide. In addition to the generally less desirable nature of the use of catalysts in the oxide form, therefore, it may be necessary to convert the iron oxide catalyst to iron metal form as a separate and necessary additional step of the cyclic process. Such a requirement would, of course, change the process from one having two essential chemistry steps, repeated on a cyclic basis, to a process having three essential chemistry steps. As indicated above, the economic and technical advantages of the inherently cyclic process of the invention would not be realized in embodiments of commercial operations in which iron, in such oxide form, is employed as the disproportionation catalyst.

As indicated above, inert gases present in the carbon monoxide-containing feed gas stream, together with gases formed during carbon monoxide decomposition, are vented from the reaction zone in which a surface layer of active surface carbon is deposited on the disproportionation catalyst. As a result, the carbon values in the carbon monoxide that are to be converted to methane are separated from said inert gases inherently in the practice of the invention. No prior concentration of the carbon monoxide present in dilute carbon monoxide-containing gas streams, and no separation of said carbon monoxide from inert gases such as nitrogen and argon present in said gas streams, is required. It is such requirements and the cost thereof that effectively preclude the use of dilute carbon monoxide-containing gas streams in prior art methanation techniques. The present invention achieves, in effect, such concentration essentially without a cost penalty compared to alternative processes that utilize gas streams containing a relatively high proportion of carbon monoxide therein to avoid the necessity for employing a prohibitively costly cryogenic or other separation of inerts. The present invention is particularly advantageous and achieves a major advance in the art in permitting the methanation of dilute carbon monoxide-containing gas streams and a relatively high proportion of inerts, e.g. the indicated gas streams containing from about 5% to about 50% by volume nitrogen.

The active surface carbon deposited on the catalyst, following the venting of inert gases therefrom, is contacted with steam or a steam-containing gas stream to convert said active surface carbon to methane and $CO_2$ in accordance with reaction (5) above. Reaction temperatures of from about 100° C. to about 400° C. may be employed, with conversion temperatures of from about 200° C. to about 350° C. being generally preferred. The conversion of active surface carbon by steam may be carried out at reaction pressures of from about 1 to about 100 atmospheres. By using high pressure steam for the active surface carbon conversion, the generation of a high pressure product gas stream is achieved without the need for expensive compression equipment and high energy consumption, further enhancing the economic attractiveness of the process. Thus, steam is the especially preferred reactant for conversion of the active surface carbon to methane in practical commercial operations in which the inherently cyclic, two step process of the invention is carried out for the methanation of CO-containing gas streams on an economically attractive basis.

The conversion of active surface carbon to methane can, less desirably, be accomplished by contacting the surface layer of said carbon with hydrogen or a hydrogen-containing gas stream under the operating conditions indicated above for conversion by steam. In this embodiment, methane is formed in accordance with the reaction:

$$C^* + 2H_2 \rightarrow CH_4. \tag{7}$$

With the hydrogen requirements of reaction (7) being supplied from CO via the water shift reaction of reaction (2), the carbon efficiency of the process can be illustrated by the overall reaction (8) below that represents the total of reactions (2), (4) and (7) as performed in the practice of the present invention:

$$4CO + 2H_2O \rightarrow 3CO_2 + CH_4. \tag{8}$$

Thus, 4 moles of CO are again required for the production of one mole of methane in the stoichiometric relationship illustrated by reaction (8). Steam, however, it preferred for the active surface carbon conversion step because of the costs associated with the generation of hydrogen. The $CO_2$ formed in said conversion by steam can readily be separated from the methane, if desired, by well known commercially available techniques to provide a relatively pure, low-cost methane product. The Benfield aqueous alkaline scrubbing process and the Shell Sulfinol and Allied Chemical Selexol solvent extraction processes are examples of commercial techniques for removing carbon dioxide and other acid gases from gas streams.

The disproportionation catalyst will typically be mixed with a catalyst support additive or with binders to assure that the catalyst has a desired combination of activity, capacity and stability. In the absence of such additives and/or binders, nickel, for example, is relatively unstable and tends to agglomerate and sinter with resultant reduction of its surface area.

It is within the scope of the invention to employ any available support additive material capable of supporting and/or dispersing the catalyst, so as to prevent agglomeration and sintering thereof, to enhance the activity and capacity of the catalyst in continuous commercial operations. Such support additives will generally be employed in varying amounts ranging from about 0.1% to about 50% by weight of additive based on the weight of catalyst composition mixture of catalyst and additive. Examples of suitable additives are zirconia, thoria, alumina, silica and mixtures thereof, although various other materials, such as rare earth oxides, may be employed for the indicated catalyst support purposes. In particular embodiments of the invention, the additive is employed in an amount within the range of from about 3% to about 15% by weight based on the weight of the catalyst composition mixture. Zirconia, alumina and silica are preferred catalyst support additives with zirconia being generally most preferred.

It will be understood that various combinations of such support additive materials, with or without binding agents, may be employed to achieve desired support and/or dispersion of the disproportionation catalyst employed in particular embodiments of the process of the invention. For example, it has been found advantageous to employ a combination of zirconia and alumina support additives. Each additive may preferably be employed in an amount within the range of from about 3% to about 30% be weight of the catalyst composition mixture of catalyst and additive, with the combination being employed in an amount up to about 50% by weight based on the weight of said catalyst composition. As indicated above, nickel is the generally preferred catalyst, with the surface area of the catalyst being generally at least about 10 $m^2/gr$, and preferrably at least about 25 $m^2/gr$, more preferably at least about 50 $m^2/gr$. Binding agents, if employed, will generally be mixed with the catalyst composition in an amount within the range of from about 5% to about 40% by weight of such binding agent based on the total weight of the catalyst composition—binder mixture. Various binding agents known in the art may be employed in a conventional manner as will readily be appreciated by those skilled in the art. Boehmite alumina, a hydrous aluminum oxide, is a convenient readily available binder.

While various catalyst-support additive combinations suitable for the purposes of the invention may readily be determined by those skilled in the art, it has been found particularly convenient to employ a coprecipitated mixture of catalyst and catalyst support additive. Thermally stable coprecipitated catalysts useful for methanation reactions have heretofore been known in the art as evidenced, for example, by the Hansford patent, U.S. Pat. No. 3,988,263 that relates to combinations of alumina with catalytic materials such as nickel. The catalyst support additive, in such embodiments, constitutes generally the hydroxide or carbonate form thereof coprecipitated with the hydroxide or carbonate of the catalyst material prior to the reduction of said catalyst hydroxide or carbonate to the active catalyst state. For purposes of the present invention, the catalyst should comprise from about 50% to about 99% of the catalyst composition mixture of catalyst and additive. Nickel and cobalt are preferred catalysts, with zirconia being the preferred catalyst support additive although it will be appreciated that alumina or other suitable support additives can also be employed.

While the invention necessarily includes two basic chemistry process steps, repeated on a cyclic basis, it will be understood that various processing steps, or unit operation steps, may be carried out incidental to the essential features of the invention. Thus, it was noted above that pretreatment of the feed may be employed to remove sulfur impurities. Likewise, any methane formed during the carbon monoxide decomposition step as a result of the presence of hydrogen or water in the feed gas may be employed for heat generation purposes to enhance the overall economics of the process. In addition, by-product carbon dioxide formed during conversion of active surface carbon with steam in accordance with reaction (5) is separated from product methane by conventional techniques. It will be understood by those skilled in the art that various other processing steps incidental to the heart of the present invention may be employed in practical applications of the invention. Accordingly, small adjustments in reaction temperature may be made, as by heating or cooling the reaction zone, and a purge gas at a desired temperature, e.g. about 240° C., may be passed through said zone to achieve a desired cooling effect. It will also be understood that, during repeated cycles of the cyclic, basically two step process of the invention, the disproportionation catalyst becomes coated with carbon that eventually reduces the efficiency of the catalyst to the point where catalyst regeneration becomes necessary or desirable. Oxidative regeneration can be employed to burn off said carbon so as to regenerate the catalyst for subsequent use in the cyclic, two step methanation process of the invention. Such regeneration can be conveniently carried out in situ in the reaction zone.

The invention is hereinafter described with reference to particular examples presented to illustrate various aspects of the subject methanation process.

EXAMPLE 1

45.4 gr, 40 ml bulk of a nickel-zirconia coprecipitated catalyst composition having a weight ratio of 7 parts nickel per part of zirconia was loaded in a glass tube and was reduced at 400° C. in a stream of helium-hydrogen of approximately 10:1 ratio at a flow rate of 150 ml/min for 16 hours. The catalyst with said nickel in metal form had a surface area of approximately 100 m$^2$/gr. The temperature was adjusted to about 200° C. and a mixture of helium and carbon monoxide in a 10:1 ratio, i.e. a dilute carbon monoxide stream, was passed through the catalyst bed at the rate of 830 ml/min for 20 minutes at one atmos pressure. The effluent was passed through solid absorbent chips to recover by-product carbon dioxide. The temperature was increased from 200° C. during this period. The absorbed $CO_2$ was found to measure 650 ml. No CO breaktrough in the effluent was observed.

The reactor temperature was adjusted to 250° C., and superheated steam in helium, at a ratio of 1:1, was passed through the bed at the rate of 360 ml/min for 13 minutes at one atmos. During the steam reaction period, the effluent was passed through the absorbent to collect additional by-product carbon dioxide. The helium carrier gas and product methane passed the absorbent zone and product methane was determined by use of vapor phase chromatographic techniques. 398 ml of additional by-product carbon dioxide were collected. The methane product was recovered in the amount of 298 ml out of a theoretical recovery of 400 ml, i.e. with an efficiency of 74%. Such conditions were observed during the 12th cycle, which was a representative cycle during the course of a 14-cycle application of the present invention in which the essential two steps thereof were repeated on a cyclic basis with no regeneration of the catalyst and with no necessity for employing any additional step for converting the catalyst from one form to another prior to commencing each succeeding cycle.

EXAMPLE 2

A nickel-zirconia catalyst composition having a 9/1 by weight nickel/zirconia ratio was heated in a 10/1 helium/hydrogen stream at 350° C. for 10 hours. After cooling in a helium stream, oxygen in helium in a 1/10 ratio was passed through the catalyst at room temperature. 18.6 of catalyst was then loaded into a stainless steel pressure reactor and heated at 250° C. for 16 hours in a 10/1 helium/hydrogen mixture at a flow rate of 150 ml/min. The thus pre-stabilized and reduced catalyst with said nickel in metal form was the employed in the process of the invention by passing a 10/1 helium/carbon monoxide gas stream through the catalyst at a rate of 830 ml/min for 20 minutes, with the reactor temperature commencing at 210° C. 600 ml of carbon dioxide was collected in an absorber as in Example 1. No CO breakthrough in the effluent of the of the carbon monoxide decomposition reaction was observed.

The reactor was then heated to 275° C. and pressurized with helium to 210 psig. Superheated pure steam, without carrier gas, was introduced into the reactor at the rate of approximately 125 ml/min for a period of 11 minutes. The effluent gas was a dispersion containing product methane, by-product carbon dioxide and helium. 162 ml of additional $CO_2$ was recovered. Product methane was recovered in the amount of 226 ml, representing a 56.5% efficiency based on the theoretical recovery of 400 ml of said product. This run was carried out as a single cycle embodiment of the embodiment.

EXAMPLE 3

A catalyst composition as in Example 2, having a nickel to zirconia ratio of 9/1, was mixed with a binder in the weight ratio of 4 parts of said catalyst composition to 1 part of binder. Boehmite alumina, i.e. aluminum oxo-hydroxide, was employed as the binder. Upon mixing, the catalyst composition-binding agent paste was peptized in $HNO_3$, extruded and fired in air at 300° C. The resulting catalyst composition was reduced and stabilized as in Example 2 and was loaded into a stainless steel reactor and heated to 350° C. in a helium-hydrogen stream for 16 hours. With the reactor temperature adjusted to 220° C., CO was metered into a $N_2$ stream in the ratio of 1/9, i.e. producing a 10% CO-containing stream. The stream was introduced into the reactor at the rate of 1.1 l/min for 6 hours. 315 ml of by-product $CO_2$ were recovered, with no CO breakthrough observed.

The reactor was pressurized at 210 psig with nitrogen, and superheated steam, as in Example 2, was introduced at the rate of 60 ml/min for 3 minutes with the reactor temperature commencing at 270° C. 655 ml of effluent gas was recovered, at which 143.5 ml was product methane. Theoretical recovery was 172.5 ml, so that the methanation efficiency was 83.2%. Such conditions were observed during the 4th cycle, which was a representative cycle in a 26 cycle run in which the two essential steps of the invention were repeated without catalyst regeneration and without any inclusion of an additional step to convert the catalyst from one form to another between any of said repeated cycles of the two step process of the invention.

EXAMPLE 4

A cobalt-zirconia catalyst composition was prepared by dissolving the corresponding nitrates in water and adding an equivalent amount of sodium hydroxide in water to form the corresponding hydroxide precipitates that were filtered, washed and dried. A 9/1 weight ratio cobalt-zirconia coprecipitated catalyst composition prepared in this manner was charged, in a 30 gr amount, in a reactor tube and reduced by heating to 400° C. in a helium/hydrogen gas stream for 16 hours. The temperature of the reactor was adjusted to 229° C. and a helium/carbon monoxide mixture, containing 5% CO by volume, was passed over the catalyst with said cobalt in metal form for a period of 5 minutes. 134 ml of by product $CO_2$ were measured.

With the reactor temperature adjusted to 247° C. at one atmo, a 30% mixture of superheated steam in helium was passed through the reactor at the reate of 220 ml/min for 5 minutes. A total of 56 ml of product methane was recovered, approaching 100% recovery. An active surface carbon loading of about 0.3% per weight of cobalt catalyst was observed, as opposed to nearly four times this catalyst loading capacity in the examples above utilizing nickel as the disproportation catalyst. The observations pertaining to this example were observed during the first cycle of a three cycle embodiment of the invention in the course of which the catalyst was not regenerated and was not converted from one form to another after each cycle and prior to repeating the two step process in the next succeeding cycle.

EXAMPLE 5

A 10 g sample of a catalyst composition as in Example 3 was loaded into a stainless steel reaction vessel equipped with stainless steel shelves upon which the extruded catalyst materials were placed in a monolayer, said vessel being designed to allow good mixing of the reagent and carrier gases therewith and efficient reaction heat removal so as to insure good reaction temperature control. The reaction vessel was then loaded into a fluidized sand bath and heated to 410° C. in a nitrogen/hydrogen stream of 20:1 volume ratio introduced at a rate of 1 l/min and maintained at 410° C. for 16 hours. After this catalyst reduction period, the catalyst was cycled 10 times at 290° C., with each cycle consisting of an exposure to a carbon monoxide-containing gas stream in order to deposit active surface carbon on the catalyst, followed by the injection of steam to convert said active surface carbon to a mixture of methane and carbon dioxide. These cycles were employed for the purpose of aging the catalyst prior to its use in the comparative studies set forth below and in Example 6.

The catalyst was then regenerated by burning off possible agglomerates of unreacted carbon with a stream containing 1% oxygen in nitrogen at 410° C., employing 1 l/min of said stream for a period of 10 hrs. The catalyst was again reduced as above following said regeneration to ensure removal of unreacted carbon.

The temperature of the reaction vessel was adjusted to 290° C., and a stream of nitrogen containing 2% carbon monoxide was introduced for a period of 7.5 minutes at the rate of 10 l/min. The first step reaction product gas was analyzed for carbon dioxide content, and a total of 232 ml of $CO_2$ was measured. The reaction vessel was pressurized to 150 psig with nitrogen following completion of the first reaction step, and was heated to 330° C., superheated steam at approximately 3 l(gas) per min. was introduced therein for 4 minutes. The effluent gas recovered was determined to contain 76 ml of methane. As the theoretical methane recovery in this steaming step was 116 ml, the methanation efficiency was 65.5%.

In the next identical cycle of the essentially two step process of the invention, carried out without regeneration or prior conversion of the catalyst, a total of 193 ml of carbon dioxide were measured in the active surface carbon deposition step, and 73 ml of product methane were recovered in the steaming, or active surface carbon conversion, step. Theoretical recovery was 96.5 ml so that the methanation efficiency was 75.6% in this second cycle.

EXAMPLE 6

The very same catalyst sample used in Example 5 was regenerated as before following completion of the second cycle of said Example 5, and the reaction vessel temperature was adjusted to 450° C. The cyclic process was then carried out as in Example 5 but with both steps carried out at 450° C. In the first process cycle at this higher temperature, 421 ml of carbon dioxide were measured in the first, or active surface carbon deposition, step, and only 7 ml of methane were measured in the second, or active surface carbon conversion, step. Thus, the methanation efficiency was found to be only 3.3%.

In a second identical processing cycle at said 450° C., 490 ml of carbon dioxide were measured in the active surface carbon deposition step, and only 7 ml of methane were recovered in the active surface carbon conversion step. Methanation efficiency in the second cycle was 2.8%.

In a third identical processing cycle, 514 ml of carbon dioxide were measured, and only 4 ml of methane were produced. The methanation efficiency of the third cycle at 450° C. was thus only 1.5%.

For practical commercial applications, it would be highly desirable to employ catalyst compositions having carbon loading capacities in excess of 0.8% together with desired stability to enhance the economic advantages obtainable in fluid bed or fixed bed applications of the methanation process herein disclosed and claimed. It will be appreciated that various catalyst compositions can be formulated that, because of the relatively low proportion of active catalyst and/or the lack of sufficient available catalyst surface area, are not adequate to achieve the methanation efficiencies capable of being achieved in the practice of the invention and to which the invention is reasonably limited as herein indicated. It will also be appreciated that the effective surface area of any given catalyst compositing may tend to decline over the course of long term, continuous operations while, nevertheless, achieving the significant advance in the art obtainable by the process of the invention, particularly in the utilization of dilute carbon monoxide-containing gas streams.

As indicated above, methane may be formed by the conversion of hydrogen or water upon passage of a carbon monoxide-containing gas stream that contains such hydrogen or water over the disproportionation catalyst. Such methane is vented from the catalyst having said surface layer of active surface carbon deposited thereon, together with the carbon dioxide formed by the decomposition of carbon monoxide and any inert gases that may be present in the gas stream. It is within the scope of the invention to subject the vented methane to combustion in a combustion zone for heat generation purposes. The heat thus generated may be employed for steam generation purposes if desired. In one embodiment, the heat thus generated may be used to generate the steam utilized for the conversion of active surface carbon to methane. This ability to effectively utilize the methane formed during the carbon monoxide decomposition step, and not readily recoverable with the product methane, further enhances the overall economic attractiveness of the methanation process of the invention. Similarly, it should be noted that any oxygen contained in the carbon monoxide-containing gas stream can be utilized, as for heat generation purposes, in-situ in the reactor during the carbon monoxide decomposition step or, if desired, in a preliminary combustion zone prior to the passage of the gas stream into the reactor for decomposition of the carbon monoxide content thereof.

It should be noted that a qualitative indication has been observed that the direct methanation of coke, i.e. the approximately thermoneutral reaction between carbon and water according to the reaction:

$$2C + 2H_2O \rightarrow CH_4 + CO_2,$$

can be catalyzed by the subject disproportionation catalysts. In reducing the catalyst to the active metal state on the carbon to be converted, a $CO_2$ $(CO)_8$/toluene solution can be absorbed onto dried charcoal pellets, heated to 100° C. to decompose the cobalt carbonyl, and placed under vacuum at 250° C. to remove the toluene. The thus-treated pellets can then be transferred under nitrogen to a suitable steel bomb, combined therein with an appropriate quantity of water and placed in said bomb in an oven at 350° C. for a few hours. Such conditions will tend to generate an autogenous pressure of about 500 psi. The bomb can then be cooled and the contents thereof measured to determine the production of methane by said direct conversion of coke and steam in the presence of said catalyst.

The process of the invention, as herein disclosed and claimed, represents a highly desirable advance in the field of methanation. It permits the production of high-Btu, pipeline-standard methane from industrial by-streams of dilute carbon monoxide not suitable for methanation by conventional methods. Many million tons of dilute by-product CO are flared each year by such basic industries as pig iron production in blast furnaces, gray iron casting, petroleum cracking, and the manufacture of carbon black. Furthermore, dilute CO-containing gas streams are available from coal gasification with air and from in-situ or underground coal gasification operations. The subject invention represents an attractive technical and economic alternative to CO concentration by cryogenic or absorption techniques prior to methanation. As shown above, the process enables the carbon monoxide in dilute CO-containing gas streams to be converted and/or separated from inert gases without the need for the costly pretreatment to concentrate and separate CO that has precluded the commercial production of methane from dilute CO-containing gas streams. The subject invention can thus be effectively utilized for the production of methane from such heretofore unsuitable sources of CO, such as the effluent from the underground gasification of coal with air, the effluent from blast furnace operations, the raw synthesis gas from the oxygen-blown gasification of coal and the like. The product methane is obtained as a low-cost, relatively pure product, capable of being produced at pipeline pressures, without reliance upon hydrogen as a reactant, with the subject process appearing to be competitive with large-scale SNG production by conventional coal gasification means. While the process is directed to the production of methane, it should also be noted in passing that various other products, such as ethane or other specific organic compounds, may conceivably be produced in various particular embodiments of the invention.

The production of methane by means of the subject invention provides a practical means for utilizing dilute CO-containing gas streams, and thus for reducing the waste of CO and for recovering and reusing such CO from industrial exhaust gases to produce low-cost, high purity methane as a replacement for natural gas. The invention constitutes, therefore, a significant advance of major importance in meeting the energy requirements of industrial societies throughout the world.

What is claimed is:

1. A cyclic two step process for the production of methane from carbon monoxide-containing gas streams comprising:
    (a) passing a carbon monoxide-containing gas stream over a catalyst present in a metal state and capable of catalyzing the disproportionation of carbon monoxide at a pressure of from about 1 to about 100 atmos and a temperature of from about 100° C. to about 350° C., said carbon monoxide thereby being decomposed to form carbon dioxide and an active surface carbon that is deposited on said catalyst, which is taken from the group consisting of nickel, cobalt, ruthenium, rhenium, and alloys thereof, said gas stream being passed over the catalyst for a time sufficient to deposit a surface layer of said active surface carbon on the catalyst essentially without the subsequent formation of inactive coke thereon;
    (b) contacting said layer of active surface carbon deposited on said catalyst present in a metal state with steam or a steam-containing gas stream at a pressure of from about 1 to about 100 atmos and a temperature of from about 100° C. to about 400° C., thereby converting said active surface carbon to methane and carbon dioxide, said methane being at least about 50% of the stoichiometric amount, the carbon thus recovered in the form of methane being at least about 12.5% of the carbon in said carbon monoxide decomposed upon contact with said disproportionation catalyst;
    (c) passing additional carbon monoxide-containing gas over said catalyst from step (b) and repeating said steps (a) and (b) on a cyclic basis said catalyst being maintained substantially in its metal state during said repeated steps (a) and (b),
whereby relatively pure methane can conveniently be produced from carbon monoxide-containing gas streams on a cyclic two step basis without the necessity for the prior concentration of said carbon monoxide and/or the separation therefrom from inert gases that may be present in said gas streams or for converting the catalyst from one form to another between said cycles.

2. The process of claim 1 in which said gas stream contains from about 1 to 100% by volume carbon monoxide.

3. The process of claim 2 in which said gas stream contains from about 5% to about 50% by volume carbon monoxide and at least about 5% by volume nitrogen.

4. The process of claim 1 in which said carbon monoxide decomposition temperature is from about 200° C. to about 350° C.

5. The process of claim 1 in which the conversion of said active surface carbon by steam is at a temperature of from about 200° C. to about 350° C.

6. The process of claim 1 in which said active surface carbon conversion is carried out at a pressure of from about 100 to about 500 psi, the use of high pressure steam permitting the generation of a high-pressure product gas stream without the need for expensive compression equipment and high energy consumption.

7. The process of claim 6 in which said active surface carbon conversion temperature is about 300° C.

8. The process of claim 1 in which said carbon monoxide-containing gas stream is passed over said catalyst essentially until CO breakthrough occurs in the gaseous effluent from said carbon monoxide decomposition reaction, thereby enhancing the amount of active surface carbon deposited while minimizing undesired formation of inactive coke.

9. The process of claim 3 in which said carbon monoxide-containing gas stream is passed over said catalyst essentially until CO breakthrough occurs in the gaseous effluent from said carbon monoxide decomposition reaction.

10. The process of claim 1 in which said catalyst comprises nickel.

11. The process of claim 1 in which said catalyst is mixed with a catalyst support additive in the amount of from about 0.1 to about 50% by weight based on the weight of said catalyst composition mixture of catalyst and additive, said catalyst having a surface area of at least about 10 m$^2$/gr.

12. The process of claim 11 in which said additive is taken from the group consisting of zirconia, thoria, alumina, silica and mixtures thereof.

13. The process of claim 12 in which said additive comprises zirconia.

14. The process of claim 12 in which said additive is employed in an amount within the range of from about 3% to about 15% by weight based on the weight of said catalyst composition mixture.

15. The process of claim 14 in which said additive comprises zirconia.

16. The process of claim 14 in which said additive comprises alumina.

17. The process of claim 14 in which said additive comprises silica.

18. The process of claim 11 in which said catalyst comprises nickel.

19. The process of claim 18 in which said nickel has a surface area of at least about 25 m$^2$/gr.

20. The process of claim 14 in which said catalyst comprises nickel.

21. The process of claim 15 in which said catalyst comprises nickel having a surface area of at least about 25 m$^2$/gr.

22. The process of claim 12 in which said additive comprises zirconia and alumina, said zirconia and alumina each being employed in an amount within the range of from about 3% to about 30% by weight, with said combination being employed in an amount up to about 50% by weight, based on the weight of the catalyst composition.

23. The process of claim 22 in which said catalyst comprises nickel.

24. The process of claim 23 in which said nickel has a surface area of at least 25 m$^2$/gr.

25. The process of claim 21 in which said nickel has a surface area of at least about 50 m$^2$/gr.

26. The process of claim 11 in which said catalyst has a surface area of at least 25 m$^2$/gr.

27. The process of claim 11 in which said catalyst composition is mixed with a binding agent in an amount within the range of from about 5% to about 40% by weight based on the total weight of the catalyst composition-binder mixture.

28. The process of claim 27 in which said catalyst comprises nickel.

29. The process of claim 28 in which said catalyst support additive comprises zirconia.

30. The process of claim 29 in which said nickel has a surface area of at least 25 m$^2$/gr.

31. The process of claim 30 in which said surface area of nickel is at least 50 m$^2$/gr.

32. The process of claim 11 in which said catalyst support additive comprises the hydroxide or carbonate thereof coprecipitated with the hydroxide or carbonate of said catalyst prior to the reduction of said catalyst hydroxide or carbonate to the active catalyst state.

33. The process of claim 32 in which said catalyst comprises nickel.

34. The process of claim 33 in which said catalyst comprises from about 50% to about 99% by weight of the catalyst composition mixture of catalyst and additive.

35. The process of claim 34 in which said catalyst support additive comprises zirconia.

36. The process of claim 35 in which said catalyst has a surface area of at least about 25 m$^2$/gr.

37. The process of claim 34 in which said catalyst support additive comprises alumina.

38. The process of claim 1 in which said carbon monoxide-containing gas stream contains hydrogen or water, said hydrogen or water being converted to methane upon passage of the gas stream over said catalyst, said methane being vented from the catalyst having said surface layer of active surface carbon deposited thereon together with said carbon dioxide and any inert gases that may be present in the gas stream.

39. The process of claim 38 and including subjecting said vented methane to combustion in a combustion zone for heat generation purposes.

40. The process of claim 39 in which said heat is employed for steam generation purposes, said steam being utilized for the conversion of active surface carbon to methane.

41. The process of claim 40 in which said catalyst comprises nickel having a surface area of at least 10 m$^2$/gr.

42. The process of claim 41 in which said catalyst support additive comprises zirconia.

43. The process of claim 42 in which said nickel has a surface area of at least about 25 m$^2$/gr.

44. The process of claim 41 in which said catalyst support additive comprises alumina.

45. The process of claim 41 in which said catalyst support additive comprises alumina and silica.

46. The process of claim 1 in which said carbon monoxide-containing gas stream comprises the effluent from the underground gasification of coal with air.

47. The process of claim 39 in which said carbon monoxide-containing gas stream comprises the effluent from the underground gasification of coal with air.

48. The process of claim 1 in which said carbon monoxide-containing gas stream comprises the effluent from blast furnace operations.

49. The process of claim 1 in which said carbon monoxide-containing gas stream comprises the raw synthesis gas from the oxygen-blown gasification of coal.

50. The process of claim 1 and including separating relatively pure methane from said carbon dioxide.

51. The process of claim 50 in which said gas stream contains from about 1% to 100% by volume carbon monoxide.

52. The process of claim 51 in which said gas stream contains from about 5% to about 50% by volume carbon monoxide and at least about 5% by volume nitrogen.

53. The process of claim 52 in which said carbon monoxide decomposition temperature is from about 200° C. to about 350° C. and in which said conversion of active surface carbon by steam is at a temperature of from about 200° C. to about 350° C.

54. The process of claim 52 in which the active surface carbon conversion is carried out at a pressure of from about 100 to about 500 psi, the use of high pressure steam permitting the generation of a high-pressure product gas stream without the need for expensive compression equipment and high energy consumption.

55. The process of claim 52 in which said catalyst comprises nickel.

56. The process of claim 55 in which said catalyst is mixed with a catalyst support additive in the amount of from about 0.1 to about 50% by weight based on the weight of said catalyst and additive, said catalyst having a surface area of at least about 10 $m^2$/gr.

57. The process of claim 56 in which said additive is taken from the group consisting of zirconia, thoria, alumina, silica and mixtures thereof.

58. The process of claim 57 in which said additive comprises zirconia.

59. The process of claim 52 in which said catalyst comprises cobalt and said additive comprises zirconia.

60. The process of claim 57 in which said catalyst has a surface area of at least 25 $m^2$/gr.

61. The process of claim 57 in which said catalyst composition is mixed with a binding agent in an amount within the range of from about 5% to about 40% by weight based on the total weight of said catalyst composition-binder mixture.

62. The process of claim 1 in which said catalyst comprises cobalt.

* * * * *